(12) United States Patent
Carrillo et al.

(10) Patent No.: US 6,649,152 B2
(45) Date of Patent: *Nov. 18, 2003

(54) ALUMINUM-ZIRCONIUM ANTIPERSPIRANT SALTS WITH HIGH PEAK 5 AL CONTENT

(75) Inventors: Angel L. Carrillo, Wellesley, MA (US); Richard Oryszczak, Palatine, IL (US); Yan-Fei Shen, Canton, MA (US)

(73) Assignee: The Gillette Company, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/138,476

(22) Filed: May 3, 2002

(65) Prior Publication Data

US 2003/0021757 A1 Jan. 30, 2003

Related U.S. Application Data

(63) Continuation of application No. 09/696,271, filed on Oct. 25, 2000, now Pat. No. 6,436,381.

(51) Int. Cl.$^7$ .............. A61K 7/32; A61K 7/34; A61K 7/38; A61K 7/00
(52) U.S. Cl. .............. 424/65; 424/66; 424/68; 424/400; 424/401; 424/DIG. 5
(58) Field of Search .............. 424/65, 66, 68, 424/400, 401, DIG. 5

(56) References Cited

U.S. PATENT DOCUMENTS

| | | | |
|---|---|---|---|
| 2,814,585 A | 11/1957 | Daley | 167/90 |
| 2,854,382 A | 9/1958 | Grad | 167/90 |
| 4,331,609 A | 5/1982 | Orr | 424/66 |
| 4,435,382 A * | 3/1984 | Shin et al. | 424/66 |
| 4,775,528 A | 10/1988 | Callaghan | 424/66 |
| 4,871,525 A | 10/1989 | Giovanniello et al. | 424/66 |
| 4,900,534 A | 2/1990 | Inward | 424/66 |
| 5,225,187 A | 7/1993 | Carmody | 424/66 |
| 5,296,623 A | 3/1994 | Katsoulis et al. | 424/66 |
| 5,330,751 A | 7/1994 | Curtin | 424/66 |
| 5,718,876 A | 2/1998 | Parekh | 424/65 |
| 5,955,064 A | 9/1999 | Giovanniello | 424/65 |
| 6,066,314 A | 5/2000 | Tang | 424/65 |
| 6,126,928 A | 10/2000 | Swaile | 424/65 |
| 6,375,937 B1 | 4/2002 | Chopra | 424/65 |

FOREIGN PATENT DOCUMENTS

| | | |
|---|---|---|
| CA | 1153313 | 9/1983 |
| EP | 653203 | 5/1995 |
| GB | 1353916 | 5/1974 |
| WO | 01/56539 | 8/2001 |
| WO | 02/34223 | 5/2002 |

OTHER PUBLICATIONS

Bretschneider et al, "Antiperspirant Efficacy", Proceedings of the 9$^{th}$ IFSCC Congress, Boston, MA 1976, pp. 263–275.
Bretschneider et al, "Physical Properties of Antiperspirant-sas Related to Their Efficacy", reprint of article from *Cosmetics and Perfumery*, Feb. 1975.
Reheis data sheet with specifications for Reach® AZP–855 (undated, but earlier than Oct. 2000).

* cited by examiner

*Primary Examiner*—Shelley A. Dodson
(74) *Attorney, Agent, or Firm*—Stephan P. Williams

(57) ABSTRACT

Disclosed are enhanced efficacy aluminum-zirconium antiperspirant salt compositions which exhibit an HPLC peak 5 area content of about 33% or more, preferably at least 45%, more preferably at least 50%, most preferably at least 55%. Especially preferred are aluminum-zirconium antiperspirant salt compositions which, in addition to the aforementioned high peak 5 content, also exhibit an HPLC peak 4 to peak 3 area ratio of at least 0.4, preferably at least 0.7. The aforementioned salt compositions will preferably have a metal (Al+Zr) to chloride (or anion) ratio of about 0.90 to about 1.00. Also disclosed are methods of making such antiperspirant salt compositions and aqueous solutions of such antiperspirant salt compositions. Further disclosed are topical compositions comprising a dermatologically acceptable carrier vehicle and a perspiration reducing effective amount of an aluminum-zirconium antiperspirant salt composition as described above.

25 Claims, 1 Drawing Sheet

US 6,649,152 B2

ALUMINUM-ZIRCONIUM ANTIPERSPIRANT SALTS WITH HIGH PEAK 5 AL CONTENT

CROSS-REFERENCE TO RELATED APPLICATION

This application is a continuation of application Ser. No. 09/696,271 filed Oct. 25, 2000, now U.S. Pat. No. 6,436,381.

BACKGROUND OF THE INVENTION

The present invention relates to aluminum-zirconium antiperspirant salts with high peak 5 aluminum content. The present invention also embraces methods of making these antiperspirant salts and compositions containing these antiperspirant salts.

Aluminum-zirconium antiperspirant salts have been known for several decades. See, for example, U.S. Pat. No. 2,814,585 (Daley), U.S. Pat. No. 2,854,382 (Grad), GB 1,353,916 (Bolich), U.S. Pat. No. 4,331,609 (Orr), U.S. Pat. No. 4,775,528 (Callaghan), U.S. Pat. No. 4,871,525 (Giovanniello), U.S. Pat. No. 4,900,534 (Inward), U.S. Pat. No. 5,225,187 (Carmody), U.S. Pat. No. 5,296,623 (Katsoulis), U.S. Pat. No. 5,330,751 (Curtin), EP 653,203 (Rosenberg), U.S. Pat. No. 5,718,876 (Parekh) and U.S. Pat. No. 5,955,064 (Giovanniello). Some of these aluminum-zirconium antiperspirant salts are described as having enhanced efficacy, which means that they provide greater sweat reduction than conventional antiperspirant salts.

The enhanced efficacy salts are typically differentiated from conventional antiperspirant salts by reference to the various aluminum peaks that can be identified when the salt is analyzed by size exclusion chromatography, typically HPLC (high pressure liquid chromatography). A suitable chromatographic technique must be capable of resolving the Al into at least four distinct peaks (labeled peaks 2 (or 1+2), 3, 4 and 5,), such as is shown in U.S. Pat. No. 5,330,751. Up to now, the enhanced efficacy salts have been described as having an increased peak 4 content or an increased peak 4 to peak 3 ratio compared to conventional salts. (In some cases, enhanced salts have been described as having increased "band III" content by some authors, depending on the chromatographic technique and nomenclature employed. Generally, bands I, II, III and IV of one system correspond to peaks 1+2 (band I), 3, 4 and 5 of the other system.) Typically, the known enhanced efficacy salts (measured as 10% solutions) have an HPLC peak 4 to peak 3 area ratio of 0.5 or higher, preferably at least 0.7, with at least 70%, preferably at least 80%, of the aluminum contained in peaks 3 and 4. Thus, the enhanced salts will typically have a peak 4 content of at least 30% of the total aluminum contained in all the peaks (measured by peak area). In contrast, conventional non-enhanced antiperspirant salts have a negligible peak 4 content or a peak 4 to 3 area ratio less than 0.2, typically about 0.1.

Up to now, no one has suggested that peak 5 content plays any role in promoting the efficacy of antiperspirant salts. Aluminum antiperspirant salts are available as 2/3, 3/4, and 5/6 aluminum chlorohydrate ("ACH") depending on the Al:Cl ratio (Al:Cl≈1, 1.7 and 2, respectively). While 2/3 ACH has a higher peak 5 content (typically greater than 50%) than 5/6 ACH (typically under 10%), it is not known to have greater antiperspirant efficacy. (See, for example, Bretschneider et al, "Antiperspirant Efficacy", in Proceedings of the 9$^{th}$ IFSCC Congress, Boston, Mass. 1976, pp. 263–75.) In fact, 5/6 ACH is the form used virtually exclusively in commercial antiperspirant products which contain ACH.

Of course, the most widely used antiperspirant products contain aluminum-zirconium salts because they are more efficacious, especially the enhanced forms, as described above, with high peak 4 to peak 3 ratio. Prior to the discovery of the enhanced Al—Zr salts, U.S. Pat. No. 4,331,609 suggested that Al—Zr salts with a metal to chloride ratio below about 1.3 (e.g., 1.25) may be more efficacious than salts with a higher metal to chloride ratio. However, this efficacy claim does not appear to have gained acceptance in the industry because salts with low metal to chloride ratios are not believed to have been produced in commercial quantities, at least not to any significant extent. More recently, U.S. Pat. No. 6,126,928 described certain polyhydric alcohol solutions of the salts described in the aforementioned '609 patent.

Generally, all of the commercially used aluminum-zirconium antiperspirant salts have a peak 5 content of less than 25%, more typically less than 10%. Recently, Westwood Chemical has introduced an aqueous aluminum-zirconium chlorohydrate solution (sold under the tradename WZR 35BX3), which is said to have stable viscosity (i.e. viscosity does not increase significantly during normal storage) and appears to be made in accordance with U.S. Pat. No. 5,955,064. This salt has a somewhat elevated peak 5 content in the 20–25% range and a relatively low peak 4 content, typically less than 15%.

The enhanced efficacy aluminum-zirconium antiperspirant salts which are currently available commercially have one significant drawback. They are unstable in aqueous solution, where they rapidly revert back to their non-enhanced state (for example, as evidenced by a significant drop in the HPLC peak 4 to peak 3 area ratio). Consequently, these enhanced antiperspirant salts are generally only available in powder form and must be formulated into finished formulations as suspended powders in order to retain their enhanced efficacy. One solution to this problem is disclosed in U.S. Pat. No. 6,042,816, where stable aqueous solutions are prepared containing a calcium salt in addition to the antiperspirant salt and an amino acid.

It would be highly desirable to provide enhanced efficacy aluminum-zirconium antiperspirant salts which are stable in aqueous solution. This would make it possible to use the enhanced salts in finished formulations that require an aqueous salt form, such as the currently attractive clear gel compositions which have been successfully introduced in recent years. It would also be highly desirable to provide an aluminum-zirconium antiperspirant salt which has even greater antiperspirant efficacy than those currently available.

SUMMARY OF THE INVENTION

The present invention embraces enhanced efficacy aluminum-zirconium antiperspirant salt compositions which exhibit an HPLC peak 5 area content of about 33% or more, preferably at least 45%, more preferably at least 50%, most preferably at least 55%. Especially preferred are aluminum-zirconium antiperspirant salt compositions which, in addition to the aforementioned high peak 5 content, also exhibit an HPLC peak 4 to peak 3 area ratio of at least 0.4, preferably at least 0.7, most preferably at least 0.9. The aforementioned salt compositions will preferably have a metal (Al+Zr) to chloride (or anion) ratio of about 0.90 to about 1.00, more preferably about 0.90 to about 0.98, most preferably about 0.90 to about 0.96. The present invention also embraces methods of making such antiperspirant salt compositions and aqueous solutions of such antiperspirant salt compositions. The present invention further embraces topical compositions comprising a dermatologically acceptable carrier and a perspiration reducing effective amount of an aluminum-zirconium antiperspirant salt composition as described above.

It has been surprisingly found that aluminum-zirconium antiperspirant salts with high peak 5 content (i.e. greater than 33%, preferably greater than 45%) are at least equivalent in antiperspirant efficacy to currently available enhanced efficacy salts (with high peak 4 content) in powder form. However, unlike the currently available enhanced salts which lose efficacy in aqueous solution, the high peak 5 salts maintain their enhanced efficacy as aqueous solutions. Moreover, if the high peak 5 salts also have a peak 4 to 3 area ratio of at least 0.4, they have even greater antiperspirant efficacy than currently available enhanced salts. This is very surprising because, although such salts have a high peak 4 to 3 ratio, they have a much lower total peak 4 content than conventional enhanced salts because most of the aluminum is present in peak 5. Conventional enhanced Al—Zr salts typically have at least 70%, more typically about 80% to 90%, of the aluminum in peaks 3 and 4. The salts of the present invention, with high peak 5 content, have less than 67%, typically about 20% to about 50%, of the aluminum in peaks 3 and 4.

DETAILED DESCRIPTION OF THE INVENTION

Figure 1:
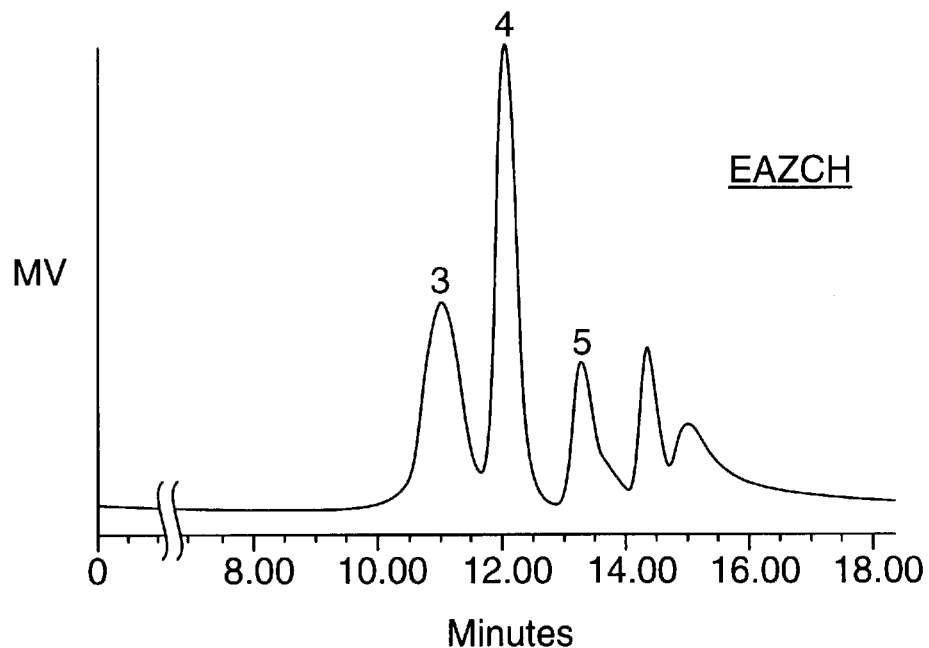
FIG. 1 is an HPLC chromatogram of a conventional enhanced efficacy aluminum-zirconium tetrachlorohydrate-gly antiperspirant salt (Al:Zr=3.6; M:Cl=1.4; peak 4:3=1.3; peak 5=17%).

The present invention embraces enhanced efficacy aluminum-zirconium antiperspirant salt compositions which, when analyzed by HPLC at about 10% (USP) concentration in water, exhibit an HPLC peak 5 area content of at least 33% or more, preferably at least 45% or more, more preferably at least 50% or more, most preferably at least 55% or more (up to about 80%, or even as high as 90%), based on the total aluminum in the salt (as shown in HPLC peaks 2 to 5). The Al—Zr salts will generally have the empirical formula $Al_nZr(OH)_{[3n+4-m(n+1)]}(X)_{[m(n+1)]}(AA)_q$ where X is Cl, Br, I or $NO_3$, preferably Cl; n is 2.0 to 10.0, preferably 3.0 to 8.0; m is 0.48 to 1.11 (which corresponds to a metal (Al+Zr) to anion (X) ratio M:X=2.1-0.9), preferably about 1.00 to about 1.11 (which corresponds to M:X=1.00-0.90), more preferably about 1.02 to about 1.11 (which corresponds to M:X=0.98-0.90), and most preferably about 1.04 to about 1.11 (which corresponds to M:X=0.96-0.90); q is about 0.8 to about 4.0, preferably about 1.0 to 2.0; and AA is an amino acid such as glycine, alanine, valine, serine, leucine, or aminobutyric acid, preferably glycine. These salts also generally have some water of hydration associated with them, typically on the order of 1 to 5 moles per mole of salt (typically, about 1% to about 16%, more typically about 4% to about 13% by weight). A preferred antiperspirant salt is an aluminum-zirconium chlorohydrate (i.e. X is Cl), more preferably an aluminum-zirconium tetrachlorohydrate (Al:Zr=2-6; M:Cl=0.9-1.5) or aluminum-zirconium octachlorohydrate (Al:Zr=6-10; M:Cl=0.9-1.5), especially one with a metal to chloride ratio of about 0.90 to 1.00.

In addition to having a high peak 5 content, it is also preferred, for maximum efficacy, that the Al—Zr salt have an HPLC peak 4 to peak 3 area ratio of at least 0.4, preferably at least 0.7, and most preferably at least 0.9. Generally, a substantial portion of the balance of the aluminum not contained in peak 5 should be present in peaks 3 and 4 (that is, substantially all of the aluminum is found in peaks 3, 4 and 5). Thus, about 15% to about 67%, preferably about 20% to about 50%, of the aluminum will be present in peaks 3 and 4. In other words, the HPLC peak 3 plus peak 4 areas will comprise about 15% to about 67%, preferably about 20% to about 55%, more preferably about 20% to about 50%, of HPLC peaks 2 to 5.

The Al—Zr salt compositions of the present invention are manufactured by mixing an aqueous solution of an aluminum antiperspirant salt (preferably an enhanced aluminum antiperspirant salt as described below) with an aqueous solution of a zirconium antiperspirant salt, each salt being present in an amount to provide the desired Al:Zr molar ratio, then adjusting the metal:anion (M:X) ratio, if necessary, by addition of an appropriate amount of HX. In order to drive the conversion of the aluminum polymer species toward the lowest molecular weight species which is found in peak 5, it is preferred to maintain a low metal (Al+Zr) to anion (X) ratio, typically M:X<1 (e.g. 0.90 to 1.00, preferably 0.90 to 0.98), during the mixing of the aluminum and zirconium salt solutions. Typically the conversion will take about 0.5 to 5 hours at room temperature (20–25° C.). The aqueous solution of Al—Zr salt with high peak 5 content may be used or stored as an aqueous solution, or it may be spray dried or vacuum dried to obtain the salt in solid powder form. Preferably, the salt will be dried to a solid while the peak 4:3 area ratio is above 0.4 to obtain a salt with maximum efficacy. Since the peak 4:3 ratio will decrease with time in solution, while the peak 5 content increases, it is a simple matter to monitor the Al peak content via HPLC over time and select a point to dry the salt where both the peak 5 content and the peak 4:3 ratio are at optimum high levels.

Preferred aluminum salts for use as starting materials are those having the general formula $Al_2(OH)_{6-a}X_a$ wherein X is Cl, Br, I or $NO_3$, and a is about 0.3 to about 5, preferably about 0.8 to about 2.5, more preferably about 1 to about 2 (such that the Al to X mole ratio is about 0.9:1 to about 2.1:1). These salts generally have some water of hydration associated with them, typically on the order of 1 to 6 moles per mole of salt. Most preferably, the aluminum salt is aluminum chlorohydrate (i.e. X is Cl in the above formula), especially 5/6 basic aluminum chlorohydrate where a is about 1, such that the aluminum to chlorine mole ratio is about 1.9:1 to 2.1:1, typically about 1.95:1. Aluminum chlorohydrate is referred to as "ACH" herein.

Preferably, the ACH is an enhanced efficacy form, sometimes written as ACH', which has an HPLC peak 4 to peak 3 area ratio of at least 0.5, preferably at least 0.7, with at least 70%, preferably at least 80%, of the aluminum contained in peaks 3 and 4. The enhanced efficacy aluminum chlorohydrates are readily made by heating a dilute ACH solution (e.g. about 10% salt concentration by weight) at about 80–100° C. for about 4 to 20 hours. It has been found that the greatest antiperspirant efficacy in the final Al—Zr antiperspirant salt with high peak 5 can be obtained when an enhanced efficacy aluminum antiperspirant salt is used as one of the starting materials.

Preferred zirconium salts for use as starting materials are those having the general formula $Zr(OH)_{4-b}X_b$ wherein X is Cl, Br, I, or $NO_3$, preferably Cl; and b is about 0.7 to about 4.0, preferably about 2.2 to about 4.0 (i.e., Zr:X≈0.45-0.25), more preferably about 3.4 to about 3.8 (Zr:X≈0.29-0.26). Although written for convenience as $Zr(OH)_{4-b}X_b$, this salt is intended to include the well-known zirconyl oxychloride and zirconyl hydroxychloride, which is also often written as $ZrO(OH)_{2-b}Cl_b$ (where b, in this instance, is about 1 to 2). The zirconium salts also generally have some water of hydration associated with them, typically on the order of 1 to 7 moles per mole of salt. In addition, the zirconium salt will contain an amino acid, as described above, to prevent gellation. Preferably the zirconium salt is zirconyl hydroxychloride of the formula $Zr(OH)_{4-b}Cl_b$ wherein b is about 0.7 to about 4.0, preferably about 2.2 to about 4.0 (i.e., Zr:Cl≈0.45-0.25), more preferably about 3.4 to about 4.0 (Zr:Cl≈0.29-0.25), most preferably about 3.4 to about 3.8 (Zr:Cl≈0.29-0.26). Zirconium salts with a low Zr:X ratio are preferred because such salts tend to have a lower molecular weight than other zirconium salts. It is theorized that the use of low molecular weight zirconium salts results in higher antiperspirant efficacy in the final Al—Zr salt. In addition, the use of zirconium salts with a low Zr:X ratio also facilitates the manufacture of the preferred Al—Zr salt with a low metal:X ratio.

As an alternative to or in conjunction with the above-described aluminum and zirconium salts, it is also possible to employ aluminum chloride ($AlC_3$) and/or zirconium basic carbonate ($Zr_2(OH)_4(CO_3)_2 \cdot nH_2O$) as starting materials, provided that the molar ratio of the various reactants is adjusted to arrive at the desired molar ratio of the aluminum, zirconium, hydroxyl and chloride moieties in the final Al—Zr salt prepared.

A preferred high peak 5 enhanced salt is aluminum-zirconium chlorohydrate (i.e. X is Cl), referred to herein as "$E^5AZCH$", which has an Al:Zr ratio of about 2 to about 10 and a metal:Cl ratio of 0.90 to 1.00, preferably 0.90 to 0.98. This salt will exhibit an HPLC peak 5 area content of about 45% or more, preferably at least 50% or more, more preferably at least 55% or more, up to about 90%, based on the total aluminum in the salt. To achieve maximum efficacy, this salt will also preferably have an HPLC peak 4 to peak 3 area ratio of at least 0.4, more preferably at least 0.7, and most preferably at least 0.9. It has been surprisingly found that such a salt has superior antiperspirant efficacy, and more surprisingly will maintain its superior antiperspirant efficacy, even when stored as an aqueous solution. This is a distinct advantage over previously known enhanced antiperspirant salts, whose efficacy deteriorates in aqueous solution.

The antiperspirant salts of the present invention may be formulated into topical compositions such as liquids (e.g., for roll-on or porous applicators), lotions, creams, gels, soft-solids, solid sticks, etc. Such compositions will comprise the antiperspirant salt in a perspiration reducing effective amount and a dermatologically acceptable carrier.

In particular, aqueous solutions of these antiperspirant salts may be directly utilized in oil-in-water and water-in-oil emulsions, such as the currently popular clear gel formulations, or in other aqueous based compositions such as aqueous based roll-ons. Preferred aqueous liquid compositions will comprise about 8% to about 45% (USP) by weight, preferably about 18% to about 38% (USP) by weight, antiperspirant salt and about 20% to about 90%, preferably about 45% to about 80%, water, such aqueous compositions optionally including other water soluble cosmetic ingredients (e.g. ethanol or polyhydric alcohol). These aqueous solutions may be stored indefinitely without significant loss of efficacy, unlike solutions of conventional enhanced efficacy salts, and may be diluted to an appropriate concentration (e.g. 6%–22% USP) for topical application when formulated into a commercial product.

It is also possible to make a solution of $E^5AZCH$ in a liquid polyhydric alcohol such as propylene glycol. The liquid polyhydric alcohol will typically have from three to six carbon atoms and from two to six hydroxyl groups. Such a solution may be readily obtained by adding the polyhydric alcohol to an aqueous solution of $E^5AZCH$ as described above, then evaporating off the water under vacuum (see, for example, U.S. Pat. No. 5,643,558). Such a polyhydric alcohol composition may advantageously comprise about 8% to about 45% (USP) of said antiperspirant salt. This product can then be readily formulated into topical antiperspirant compositions which use a polyhydric alcohol vehicle, such as clear sticks gelled with dibenzylidene sorbitol or other gellants (see, for example, U.S. Pat. No. 5,705,171).

It is especially preferred to produce the $E^5AZCH$ salts of the present invention in solid powder form, for example by spray drying or vacuum drying the aqueous solution in which these salts are produced. The powdered antiperspirant salts may then be formulated into any known type of topical composition which utilizes powdered salts, including, in particular, liquid roll-on, cream, soft solid and solid stick formulations in which the powdered salt is suspended in an anhydrous, dermatologically acceptable carrier, particularly a carrier comprising a silicone (e.g. cyclomethicone, dimethicone, etc.), typically at a concentration of about 6% to about 22% (USP) active by weight.

The present invention also embraces a method of inhibiting or reducing perspiration by topically applying an effective amount of an antiperspirant composition as described herein to the skin of a human, preferably to the axilla, where such reduction in perspiration is desired by the user. An effective amount is that amount which provides at least a 20% sweat reduction, preferably at least a 40% sweat reduction, when tested in accordance with a standard hot room thermal efficacy protocol, and most preferably that amount which reduces perspiration to a degree that is noticeable by the user. Typically, the amount of antiperspirant composition applied will range from about 0.1 gram to about 1.0 gram per axilla depending on the formulation or such amount as will deliver about 0.01 to about 0.25 gram of antiperspirant active per axilla.

The present invention may be further illustrated by the following examples in which the parts and percentages are by weight. In these examples, the abbreviation ACH means standard efficacy (i.e. non-enhanced) 5/6 basic aluminum chlorohydrate with an Al:Cl ratio of about 1.95. Unless otherwise stated, the ACH used in the examples has a concentration of about 42% USP active (nominally 50% by weight). The abbreviation ACH' means an enhanced efficacy form of this salt, that is one having an HPLC peak 4 to peak 3 area ratio of at least 0.7 with at least 80% of the aluminum contained in peaks 3 and 4. The ACH' is made by diluting ACH with water to form a solution of about 10% concentration, heating the dilute ACH solution at about 85° C. for about 16 hours, then rapidly concentrating the ACH' by vacuum evaporation (for example, using a falling film evaporator) to a concentration of about 42% USP active and cooling to room temperature. The ACH' must be used within several hours of preparation, preferably as soon as possible after preparation, in order to insure that it has the desired high peak 4 to peak 3 ratio.

The abbreviation ZHCG means zirconyl hydroxy chloride-glycine (Zr:Gly≈1). When referring to this material, the Zr:Cl ratio (e.g. Zr:Cl=0.28) will be indicated in parentheses following the abbreviation. The ZHCG may be prepared by reacting zirconium basic carbonate with an appropriate amount of HCl to achieve the desired Zr:Cl ratio, then adding the appropriate amount of glycine. The aqueous ZHCG used in the examples has a Zr content of about 8% (Zr:Cl 0.26) to about 19% (Zr:Cl 1.1) by weight Zr.

The abbreviation AZCH means aluminum-zirconium chlorohydrate-gly (standard efficacy), EAZCH means a conventional enhanced efficacy AZCH with high peak 4:3 ratio, and E$^5$AZCH means an enhanced efficacy AZCH of the present invention with high peak 5.

COMPARATIVE EXAMPLE

In accordance with the technique described in U.S. Pat. No. 4,775,528, freshly prepared aqueous ACH' solution is mixed with aqueous ZHCG$^a$ (Zr:Cl=0.67) in the appropriate molar ratio to provide an aqueous solution of enhanced efficacy aluminum-zirconium tetrachlorohydrate (~33% USP) with an Al:Zr mole ratio of about 3.6 and a M:Cl mole ratio of about 1.4. This solution is spray dried to obtain the EAZCH salt in solid powder form. A sample of this antiperspirant salt, when dissolved in water at about 10% concentration and analyzed by HPLC within a few minutes of preparation, produces a chromatogram as shown in FIG. 1. From this chromatogram, it can be seen that more than 80% of the aluminum is contained in peaks 3 and 4, with the peak 4:3 area ratio being about 1.3, while the amount of peak 5 aluminum is about 17% of the total aluminum. As is well-known, this salt cannot be usefully employed in aqueous form because the peak 4:3 ratio deteriorates very quickly, thus reverting to a standard efficacy salt.

The above-described enhanced efficacy salt may be tested for thermal efficacy (i.e. hot room sweat reduction) using volunteer panelists in a standard hot room protocol. The test product (vehicle plus enhanced efficacy salt) is applied to one axilla and control product (vehicle only or vehicle plus standard efficacy antiperspirant salt) is applied to the other axilla. The above-described enhanced efficacy salt typically provides a sweat reduction of about 57–62% versus about 47–52% obtained with standard efficacy salt, when suspended as an 18–19% USP active in a liquid volatile silicone carrier vehicle. Also, a freshly prepared aqueous solution of the above-described enhanced efficacy salt (20% USP active) typically provides a sweat reduction of about 63–69% versus about 48–54% obtained with standard efficacy salt in aqueous solution at the same concentration.

EXAMPLE 1

Figure 2:
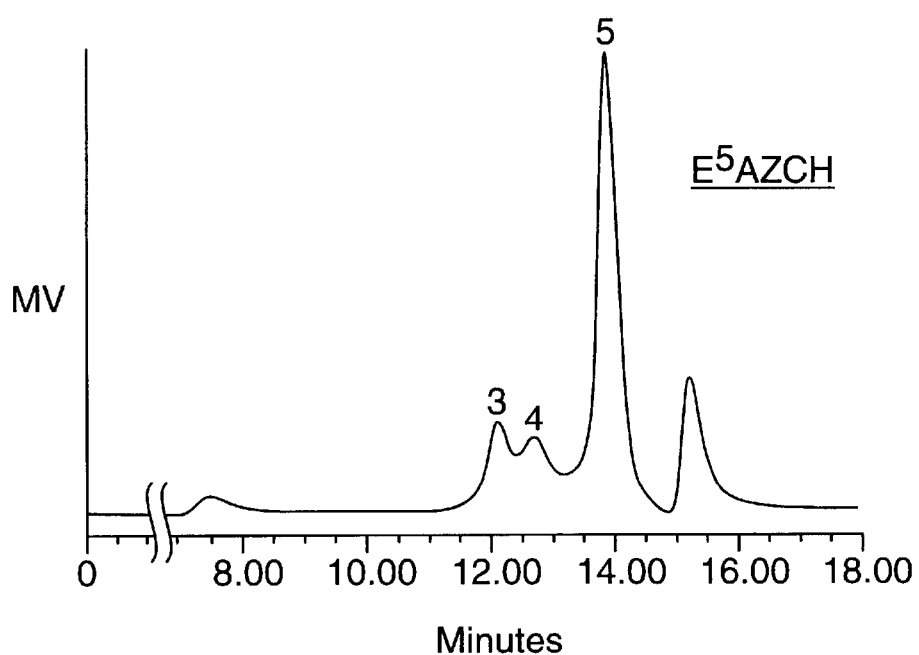
FIG. 2 is an HPLC chromatogram of a high peak 5 enhanced efficacy aluminum-zirconium octachlorohydrate-gly antiperspirant salt of the present invention (Al:Zr=6.2; M:Cl=0.95; peak 4:3=1.1; peak 5=71.7%).

Freshly prepared aqueous ACH' solution (or in one case, sample H, standard ACH solution) is mixed with aqueous ZHCG solution (as defined below) in the appropriate molar ratio to provide the desired Al:Zr ratio along with sufficient HCl, as needed, to provide the desired M:Cl ratio, thus forming aqueous solutions of enhanced efficacy aluminum-zirconium chlorohydrates (about 30–35% USP active) with Al:Zr mole ratios, M:Cl mole ratios, and HPLC peaks as shown in Table 1 below. The various ZHCG solutions used are as follows: ZHCG$^b$ (Zr:Cl=0.26-0.28), ZHCG$^c$ (Zr:Cl= 0.44-0.45), and ZHCG$^d$ (Zr:Cl=0.44-0.45), the ZHCG$^d$ being a blend of about 60 parts ZHCG$^b$ and about 40 parts ZHCG$^f$ (Zr:Cl=1.05-1.10). A portion of each antiperspirant salt solution is retained for further testing, and the remainder is spray dried to recover the antiperspirant salt as a powder. Antiperspirant salt B, when diluted to about 10% concentration, produces an HPLC chromatogram as shown in FIG. 2.

TABLE 1

Enhanced Al—Zr Salts With High Peak 5

| E$^5$AZCH | ZHCG | Al:Zr | M:Cl | Peak 5 | Peak 4:3 |
|---|---|---|---|---|---|
| A | b | 10 | 0.94 | 53.9 | 0.41 |
| B$^1$ | b | 6.2 | 0.95 | 71.7 | 1.1 |
| C | b | 10 | 0.94 | 53.7 | 0.46 |
| D | d | 2 | 0.92 | 51.8 | 1.9 |
| E | c | 2.1 | 0.95 | 48.5 | 2.4 |
| F | d | 2 | 0.92 | 57.7 | 1.72 |
| G$^2$ | d | 2 | 0.9 | 74.7 | 0.17 |
| H$^3$ | d$^4$ | 2 | 0.94 | 57.2 | 0.2 |
| J | b | 4.6 | 0.96 | 50.0 | 1.7 |
| K | b | 7.8 | 1.15 | 33.7 | 2.0 |

$^1$Aged 1.5 years as aqueous solution (~33% USP)
$^2$Heated at 70° C. for 24 hours after mixing components to reduce the peak 4:3 ratio
$^3$Made with standard ACH (peak 4:3 ratio <0.2)
$^4$Zr:Cl = 0.47 by blending ZHCG$^b$ (Zr:Cl = 0.28) and ZHCG$^a$ (Zr:Cl = 0.67)

EXAMPLE 2

The above-described high peak 5 enhanced efficacy salts of Example 1 are tested for thermal efficacy (i.e. hot room sweat reduction) using volunteer panelists in a standard hot room protocol. The test product is applied to one axilla and control product is applied to the other axilla in an AvB comparison. In all cases, the test product comprises vehicle (as described below) plus high peak 5 enhanced efficacy salt (E$^5$AZCH). The control product comprises vehicle plus conventional enhanced efficacy (high peak 4:3) antiperspirant salt (EAZCH), except where the vehicle is a clear gel formulation, in which case a standard efficacy salt (AZCH) is used because of the instability of the conventional enhanced salt in aqueous formulations. To counteract this instability, the formulation identified as "Aqueous" below, is freshly prepared with powdered EAZCH just prior to being tested. The formulations tested are set out below and the results are shown in Table 2. The results are reported as the average sweat reduction ("S.R.") gain over the control (i.e. the absolute percentage point increase in sweat reduction over the control).

| Aaueous | Roll-On |
|---|---|
| 20% USP AP active | 20.0% AP active |
| q.s. water | 75.1% Cyclomethicone |
| | 3.5% Quaternium-18 hectorite |
| | 1.0% Propylene carbonate |
| | .4% Fragrance |
| Clear Gel | Solid |
| 23.5% AP active | 23.5% AP active |
| 39.8% Water | 51.9% Cyclomethicone |
| 8.7% Propylene Glycol | 13.5% Stearyl alcohol |
| 10.0% Ethanol | 3.0% Hydrogenated castor oil |
| 9.7% Dimethicone | 4.0% Myristyl myristate |
| 8.1% Cyclomethicone (and) Dimethicone copolyol | 1.8% Silica |
| | 2.3% Fragrance/Silk Powder |
| 0.2% Fragrance | |

TABLE 2

Thermal Efficacy of Al—Zr Salts With High Peak 5

| E⁵AZCH | Vehicle | Control | Avg. S.R. Gain Over Control |
|---|---|---|---|
| A | Roll-On | EAZCH | 5.8 (p = 0.0001) |
| B | Aqueous[1] | EAZCH | 7.0 (p = 0.004) |
| C | Aqueous | EAZCH | 4.2 (p = 0.025) |
| C | Clear Gel | AZCH | 15.9 (p = 0.0001) |
| C | Clear Gel[2] | AZCH | 13.3 (p = 0.0001) |
| D | Aqueous | EAZCH | 5.9 (p = 0.0001) |
| D | Aqueous | EAZCH | 4.6 (p = 0.002) |
| D | Roll-On | EAZCH | 8.7 (p = 0.0001) |
| E | Aqueous | EAZCH | 1.3 (N.S.)[4] |
| F | Aqueous | EAZCH | 4.5 (p = 0.059) |
| F | Solid | EAZCH | 4.0 (p = 0.012) |
| G[3] | Solid | EAZCH | 2.1 (N.S.) |
| H[3] | Aqueous | EAZCH | 0.3 (N.S.) |
| J | Aqueous | EAZCH | 4.3 (p = 0.001) |
| K | Aqueous | EAZCH | 1.7 (N.S.) |

[1] Aged 1.5 years
[2] Aged 3 months at 45° C. (HPLC of extracted salt: peak 4:3 = 0.47; peak 5 = 65.8)
[3] Low peak 4:3 ratio (0.2)
[4] N.S. = not significant From the above data, it can be seen that the preferred enhanced antiperspirant salts of the present invention (high peak 5 and peak 4:3>0.4; e.g. salts A, B, C, D, F and J) are more efficacious than conventional enhanced antiperspirant salts (high peak 4:3 ratio, but low peak 5). This result is surprising because the amount of aluminum contained in peaks 3 and 4 of the E⁵AZCH salt is considerably reduced versus the EAZCH (<50% vs. >80%). Even more surprising is the fact that the E⁵AZCH salt (salt B) retains its superior efficacy when stored as a concentrated aqueous solution (in this case, for 1.5 years). Conventional enhanced salts lose their enhanced state in aqueous solution.

When formulated as a clear gel, the high peak 5 salt (salt C) is substantially more efficacious than the current commercial clear gel product, which must use a standard efficacy salt, and this high peak 5 salt maintains its high efficacy even after storage of the clear gel at high temperature. In addition, the high peak 5 salts with low peak 4:3 ratio (salts G and H) are surprisingly just as efficacious as the conventional enhanced salt with high peak 4:3 ratio. Such salts, while not quite as efficacious as the preferred salts, can provide a useful alternative to the currently available enhanced salts, particularly where improved efficacy is desired in aqueous based formulations where current enhanced salts cannot be used. Similarly, salt K, with only a modest peak 5 content (peak 5=33.7%) is just as efficacious as a conventional enhanced salt and could be an advantageous alternative, particularly in aqueous based formulations. Although salt E proved to be just as efficacious as the conventional enhanced salt and would thus offer the same advantage as salts G and H, it is believed that further testing would reveal that an E⁵AZCH with a peak 5 content of 48% would be somewhat more efficacious than a conventional enhanced salt.

Throughout the specification reference to HPLC analysis means that chromatograms are obtained as follows: Salt solutions are evaluated for aluminum polymer distribution by HPLC at a concentration of about 10% (USP) Al—Zr salt. If the solution to be analyzed is at a higher salt concentration, it is diluted with sufficient water to bring the salt concentration to about 10%. A 1.0 μL sample is injected into a Waters U6K injector, then pumped through a 4.6 mm×500 mm column packed with Nucleosil 100-5 silica with pore size of 100 angstroms and particle size of 5 μm (Keystone Scientific Inc.) using a 0.01M aqueous nitric acid solution as the eluant. The flow rate of the mobile phase is controlled at 0.5 mL/min with an LDC/Milton Roy Constametric-II metering pump (ThermoQuest Inc.). HPLC profiles are recorded and processed with a computerized system that includes the Millennium 32 Chromatography Manager software from Waters Corp. A Waters 2410 differential refractometer is used as the refractive index detector. The HPLC profiles are read from left to right (higher to lower molecular weight). Following this technique, peak 3 typically appears at a retention time of about 11.0–12.0 minutes ($Kd \approx 0.58-0.61$), peak 4 typically appears at a retention time of about 11.9–12.9 minutes ($Kd \approx 0.62-0.72$), and peak 5 typically appears at a retention time of about 13.3–14.0 minutes ($Kd \approx 0.83-0.91$). Naturally, of course, other HPLC techniques which use different column materials, eluants and flow rates can be used provided that they sufficiently resolve peaks 3, 4 and 5 with an acceptable degree of precision (i.e. the technique must be capable of resolving the Al into at least four distinct peaks, with the first Al peak being labeled peak 2 or peak 1+2). Obviously, such other techniques may place peaks 3, 4 and 5 at different retention times from those given above.

It should be noted that reference throughout this application to weight percent of antiperspirant salt is intended to be calculated as anhydrous weight percent in accordance with the new U.S.P. method. This calculation excludes any bound water and glycine. For aluminum-zirconium chlorohydrate, the calculation is as follows:

$$\%AZCH = \%Al\{26.98y+92.97+17.01[3y+4-(y+1)/z]+35.45(y+1)/z\}/26.98y$$

where y=Al/Zr ratio and z=metal/Cl ratio.
For reference purposes, calculation of antiperspirant salt weight percent in accordance with the U.S.P. method compares to the previously used standard industry method as follows: 50% AZCH (std)≈38.5% USP.

What is claimed is:

1. An aluminum-zirconium octachlorohydrate having a metal (Al+Zr) to chloride molar ratio of 0.90 to 1.00.

2. An aluminum-zirconium octachlorohydrate having the formula $Al_nZr(OH)_{[3n+4-m(n+1)]}(Cl)_{[m(n+1)]}(Gly)_q$ wherein n is 6.0 to 10.0, m is 1.00 to 1.11, and q is about 0.8 to about 4.0.

3. The aluminum-zirconium octachlorohydrate of claim 2 wherein q is about 1.0 to 2.0.

4. The aluminum-zirconium octachlorohydrate of claim 3 wherein m is about 1.02 to about 1.11.

5. The aluminum-zirconium octachlorohydrate of claim 3 wherein m is about 1.04 to about 1.11.

6. The aluminum-zirconium octachlorohydrate of claim 3 which, when analyzed by HPLC as a 10% aqueous solution using conditions capable of resolving the aluminum into at least four successive peaks (labeled peaks 2 to 5), exhibits an HPLC peak 5 area of at least 45% and an HPLC peak 4 to peak 3 area ratio of at least 0.4, wherein substantially all of the aluminum is found in peaks 3, 4 and 5.

7. The aluminum-zirconium octachlorohydrate of claim 2 made with a zirconium hydroxychloride of the formula $Zr(OH)_{4-b}Cl_b$ wherein b is 2.2 to 4.0 so that the Zr:Cl ratio in said zirconium hydroxychloride is between 0.45 and 0.25.

8. The aluminum-zirconium octachlorohydrate of claim 1 made with a zirconium hydroxychloride of the formula $Zr(OH)_{4-b}Cl_b$ wherein b is about 3.4 to 4.0 so that the Zr:Cl ratio in said zirconium hydroxychloride is between 0.29 and 0.25.

9. The aluminum-zirconium octachlorohydrate of claim 2, 3, 4, 5 or 6 made with a zirconium hydroxychloride of the formula $Zr(OH)_{4-b}Cl_b$, wherein b is about 3.4 to 4.0 so that the Zr:Cl ratio in said zirconium hydroxychloride is between 0.29 and 0.25.

10. The aluminum-zirconium octachlorohydrate of claim 1, 2, 3, 4, 5, 6 or 7 in solid powder form.

11. An aqueous composition comprising water and, dissolved therein, an aluminum-zirconium octachlorohydrate according to claim 1, 2, 3, 4 or 7.

12. The aqueous composition of claim 11 comprising about 8% to about 45% (USP) of said aluminum-zirconium octachlorohydrate.

13. A composition comprising a liquid polyhydric alcohol and, dissolved therein, an aluminum-zirconium octachlorohydrate according to claim 1, 2, 3, 4 or 7.

14. The composition of claim 13 comprising about 8% to about 45% (USP) of said aluminum-zirconium octachlorohydrate.

15. A clear antiperspirant gel composition comprising a water-in-oil emulsion having a water phase and an oil phase, wherein the water phase comprises an aqueous composition according to claim 11.

16. A topical antiperspirant composition comprising a dermatologically acceptable carrier and a perspiration reducing effective amount of an aluminum-zirconium octachlorohydrate according to claims 1, 2, 3, 4 or 7.

17. The topical antiperspirant composition of claim 16 wherein said carrier is an anhydrous carrier and said aluminum-zirconium octachlorohydrate is in solid powder form suspended in said anhydrous carrier.

18. The topical antiperspirant composition of claim 17 wherein said anhydrous carrier comprises a silicone.

19. The topical antiperspirant composition of claim 16 in the form of a liquid, lotion, cream, gel, soft-solid, or solid stick.

20. A method of reducing perspiration from human skin comprising applying to human skin a topical antiperspirant composition according to claim 16.

21. A method of reducing perspiration from human skin comprising applying to human skin an aluminum-zirconium octachlorohydrate according to claim 1, 2, 3, 4 or 7.

22. A method of preparing an aluminum-zirconium chlorohydrate of the formula $Al_nZr(OH)_{[3n+4-m(n+1)]}(Cl)_{[m(n+1)]}^-(Gly)_q$ wherein n is 2.0 to 10.0, m is 1.00 to 1.11, and q is about 0.8 to about 4.0, which method comprises mixing an aqueous solution of an aluminum chlorohydrate of the formula $Al_2(OH)_{6-a}Cl_a$ wherein a is about 1 to about 2, with an aqueous solution comprising glycine and a zirconium hydroxychloride of the formula $Zr(OH)_{4-b}Cl_b$ wherein b is 2.2 to 4.0, each of said aluminum chlorohydrate and zirconium hydroxychloride being present in an amount to provide an Al:Zr molar ratio of 2.0 to 10.0, and, if necessary, adjusting the metal (Al+Zr) to chloride ratio (M:Cl) to 0.90 to 1.00 by addition of an appropriate amount of aqueous HCL.

23. The method of claim 22 wherein b is about 3.4 to 4.0 in said zirconium hydroxychloride.

24. The method of claim 22 wherein said aluminum antiperspirant salt has an HPLC peak 4 to peak 3 area ratio of at least 0.5 with at least 70% of the aluminum contained in peaks 3 and 4.

25. The method of claim 22, 23 or 24 which additionally comprises drying said solution to obtain said aluminum-zirconium chlorohydrate in solid form.

* * * * *